United States Patent [19]

Shen

[11] Patent Number: 5,096,188
[45] Date of Patent: Mar. 17, 1992

[54] GAIT TRAINING BOARD WITH MAGNETS

[76] Inventor: Chin-Biao Shen, 5F-23, No. 70, Fu-Shing Rd., Taoyuan, Taiwan

[21] Appl. No.: 644,125

[22] Filed: Jan. 22, 1991

[51] Int. Cl.⁵ .................. A63B 23/04; A61H 7/00
[52] U.S. Cl. ............................... 272/96; 272/70; 600/9; 128/60
[58] Field of Search .............. 128/57, 58, 59, 60, 128/61, 62 R; 272/70, 96; 600/9, 15

[56] References Cited

U.S. PATENT DOCUMENTS

| | | | |
|---|---|---|---|
| 1,173,838 | 2/1916 | Miller | 128/57 |
| 1,965,918 | 7/1934 | Auberger | 128/57 |
| 1,981,379 | 11/1934 | Thomson et al. | 272/70 |
| 2,465,725 | 3/1949 | Herzmark | 272/96 |
| 2,476,921 | 7/1949 | Shock | 272/96 |
| 2,820,454 | 1/1950 | Wright | 272/96 |
| 3,100,483 | 8/1963 | Altmeyer et al. | 128/60 |
| 4,210,134 | 7/1980 | Okazaki et al. | 128/60 |
| 4,509,219 | 4/1985 | Yagi | 600/9 |

Primary Examiner—Robert Bahr
Assistant Examiner—Lynne A. Reichard
Attorney, Agent, or Firm—Bacon & Thomas

[57] ABSTRACT

A gait training board, including a flexible base board having a plurality of holes on the top for mounting a plurality of pebble-like convex moldings of different sizes, and a plurality of fastening elements inserted in the holes from the bottom to secure the pebble-like convex moldings in position through plug-in corrections. The pebble-like convex moldings each have a magnet fastened therein to produce magnetism over the board.

2 Claims, 3 Drawing Sheets

GAIT TRAINING BOARD WITH MAGNETS

BACKGROUND OF THE INVENTION

The present invention relates to gait training boards, and more particularly to a gait training board for exercising the foot, wherein the board can be conveniently assembled into a position of use for exercising, and thereafter collapsed to occupy less space for storage.

A conventional gait training board for exercising the foot is generally made of rigid plastic material formed by an injection molding process, and has a plurality of pebble-like raised portions in different sizes for massaging the sole of the foot when the user is walking on the board. This known structure is not satisfactory in use because of the following disadvantages:

1. Since it is made of rigid plastic, the board cannot be used on an uneven ground surface. Therefore, it must be placed on a flat ground surface for use.
2. If a plurality of such gait training boards are put together for exercising, they may inadvertently become disengaged from each other or the sharp edges of the boards may hurt the sole of the foot.
3. The pebble-like raised portions are not changeable.
4. Because the board is made of rigid plastic material, it cannot be rolled up when not in use. Therefore, storage of the board requires a large space.

SUMMARY OF THE INVENTION

According to the present invention, there is provided a gait training board which can be disassembled and rolled up to reduce storage space when it is not in use. The gait training board is comprised of a base board made of flexible plastic material and provided with a plurality of holes therethrough for mounting a plurality of pebble-like convex moldings, each of which is secured in position by a fastening element. Each fastening element has a circular column at its top and each pebble-like convex molding has a blind hole at its bottom. Therefore, each pebble-like convex molding can be conveniently and firmly secured to each fastening element by inserting the column into the blind hole to form a plug-in connection. The pebble-like convex moldings each have a magnet fastened therein, with the polarities of adjacent magnets being positioned in opposite directions to produce a magnetic field. Each pebble-like convex molding also has a notch on its bottom edge for receiving a screw driver or pry bar to permit the convex molding to be separated from its fastening element.

In comparison with the aforesaid prior art, the present invention can achieve the following advantages:

1. Because the base board of the invention is formed of flexible plastic material, it can be utilized on an uneven ground surface.
2. The pebble-like convex moldings and the fastening elements of the invention can be conveniently connected together through the plug-in connections.
3. The fastening elements each have a circular column inserted in the circular blind hole on the bottom of a corresponding pebble-like convex molding, with the circular column also serving to support the pebble-like convex molding connected thereto.
4. The pebble-like convex moldings are made in different sizes and colors, and can be adjustably arranged on the base board according to the preference of the user.
5. The pebble-like convex moldings each have a notch on the bottom edge thereof so that they can be conveniently removed from their corresponding fastening elements by a screw driver or pry bar.
6. The base board can be rolled up to reduce storage space when it is not in use.
7. The pebble-like convex moldings each have a magnet fastened therein, with the polarities of adjacent magnets being disposed in opposite directions so that a magnetic field can be produced over the base board to provide magnetic therapy for the foot of the user.

BRIEF DESCRIPTION OF THE DRAWINGS

The present invention will now be described by way of an example, with reference to the annexed drawings, in which.

DETAILED DESCRIPTION OF THE PREFERRED EMBODIMENT

Figure 1:
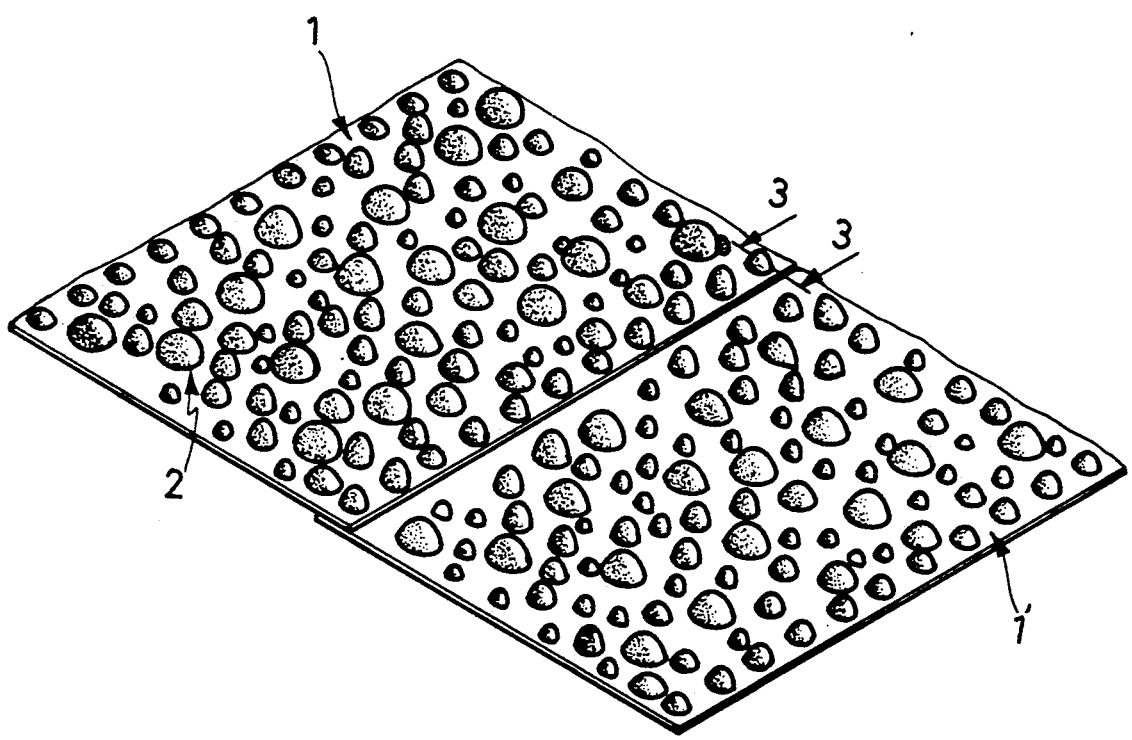
FIG. 1 is a perspective view of a gait training board according to a preferred embodiment of the invention.
Figure 2:
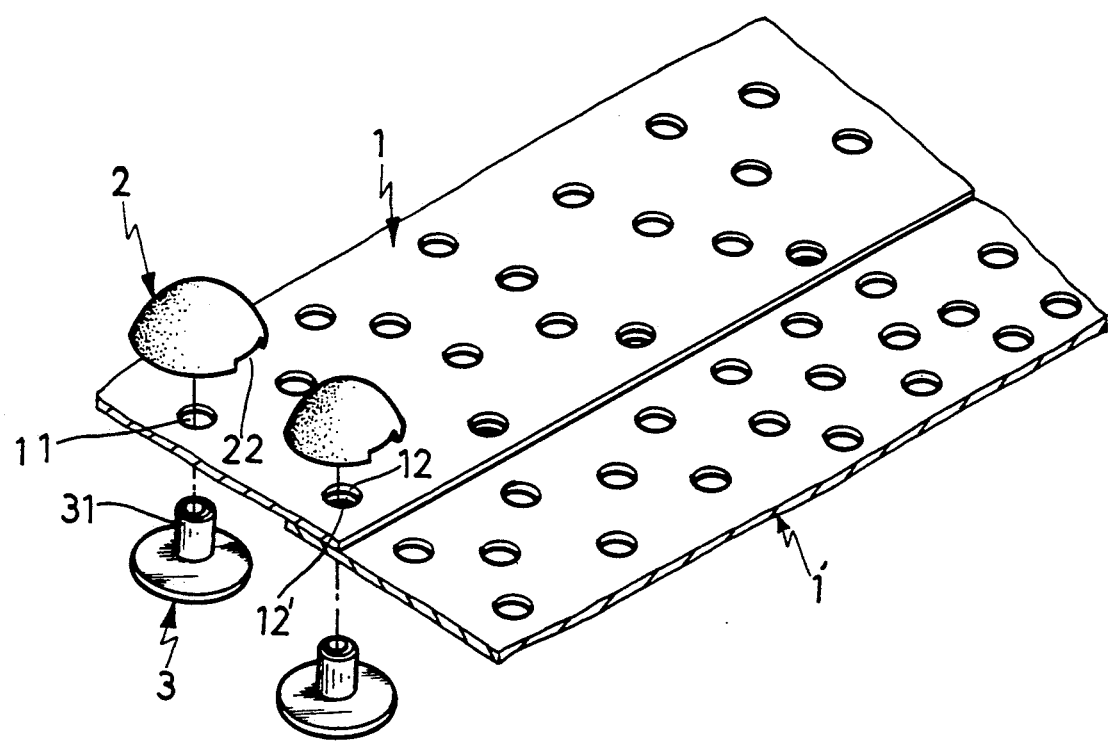
FIG. 2 is an exploded perspective view thereof.

Referring to FIGS. 1 and 2, a gait training board according to a preferred embodiment of the invention is generally comprised of at least a single base board 1 having a plurality of lines of spaced mounting holes 11 formed therethrough for mounting a plurality of pebble-like convex moldings 2 of different sizes and colors thereon, depending on the preference of the user. Each convex molding 2 is secured by a fastening element 3. When two boards 1 and 1' are desired to be secured together, as shown in FIG. 2, aligned connecting holes 12 and 12' extending along corresponding edges of boards 1 and 1' are utilized for receiving convex moldings 2 and fastening elements 3. Mounting holes 11 in boards 1 or 1' are positioned between two opposed lines of connecting holes 12 or 12'.

Each fastening element 3 has a circular column 31 extending outwardly from its top portion for inserting through either mounting hole 11 or connecting holes 12 and 12' for securing a convex molding 2 thereto. During assembly, base boards 1 and 1' are connected together by overlapping their corresponding edges to permit holes 12 of board 1 and holes 12' of base 1' to be vertically aligned. A plurality of fastening elements 3 are then inserted from the bottom of board 1' through aligned holes 12' and 12 to connect with a plurality of convex moldings 2 at the top of board 1 to firmly secure boards 1 and 1' together.

Figure 3:
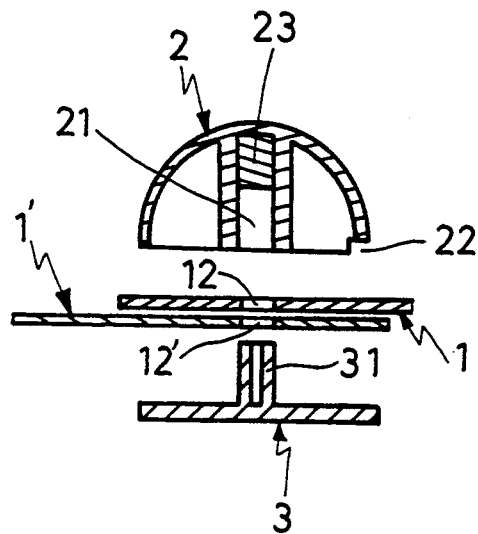
FIG. 3 is an exploded sectional view taken on the line 3—3 of FIG. 1, illustrating the internal structure of the convex molding and the fastening element.
Figure 4:
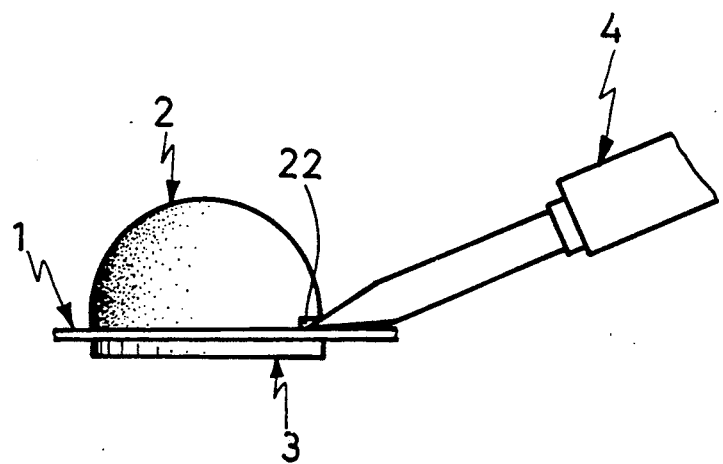
FIG. 4 is an elevational view illustrating a screw driver being used to remove a convex molding from its corresponding fastening element.

With reference to FIG. 3, the manner in which convex molding 2 and fastening element 3 are utilized to secure boards 1 and 1' together shall now be described. This is realized by inserting circular column 31 of fastening element 3 through vertically aligned holes 12' and 12 of base boards 1' and 1, respectively. Column 31 is then inserted into a circular blind hole 21 formed at the bottom of the corresponding convex molding 2. The circular column 31 has an outer diameter which is correspondingly sized to the inner diameter of the circular blind hole 21 to permit molding 2 to be firmly retained to fastening element 3. This arrangement forms a plug-in connection which is further facilitated by forming molding 2 and fastening element 3 from resilient elastic material. Furthermore, a magnet 23 may be disposed within the circular blind hole 21 of each convex molding 2. Magnet 23 is of a conventional type having opposed north and south poles. Magnets 23 are arranged in moldings 2 so that magnets 23 of adjacent moldings 2 are positioned with their opposite poles facing toward each other, thereby producing a magnetic field therebetween. In this way, adjacent magnets 23 of opposite polarity attract each other thus producing magnetism over the gait training board of the invention. This magnetism is therapeutic in that it produces physical irritation of the sole of the foot during use of the board.

I claim:

1. A gait training board comprising:
   a) a base board formed of flexible plastic material and provided with a plurality of mounting holes therethrough and a line of connecting holes therethrough;
   b) a plurality of pebble-like convex moldings, each convex molding including a circular blind hole at a bottom portion thereof and a magnet disposed within the blind hole;
   c) a plurality of fastening elements, each fastening element including a circular column extending outwardly from a top portion thereof, the circular column being dimensioned for insertion within a circular blind hole of a convex molding for securing the molding and fastening element together;
   d) the convex moldings being disposable over the mounting holes of a top side of the base board and secured thereto by inserting the circular columns of the fastening elements through the mounting holes from a bottom side of the base board into the circular blind holes of the moldings;
   e) the connecting holes being disposable in vertical overlapping alignment with the connecting holes of another base board for permitting two base boards to be connected together by inserting the circular columns of the fastening elements through the aligned connecting holes and into the circular blind holes of the convex moldings; and
   f) wherein, when the convex moldings are secured to the fastening elements, the magnets of adjacent convex moldings are positioned in opposite polarity to each other for producing a magnetic field over the board.

2. The gait training board of claim 1 wherein each convex molding includes a notch formed in a bottom edge thereof for insertion of a tool to permit removal of the convex molding from the fastening element.

* * * * *